United States Patent [19]

Hurlburt

[11] 3,986,136

[45] Oct. 12, 1976

[54] RANDOM INTERVAL GENERATORS AND METHOD OF BEHAVIOR MODIFICATION USING SAME

[76] Inventor: Russell T. Hurlburt, 22490 Edgecliff Drive, Euclid, Ohio 44123

[22] Filed: Jan. 29, 1975

[21] Appl. No.: 545,093

[52] U.S. Cl. .............................. 331/78; 35/22 R; 307/265; 328/111; 331/49; 331/55; 331/173
[51] Int. Cl.² .................................... H03K 3/84
[58] Field of Search .............. 331/78, 49, 47, 55, 331/173; 35/22 R; 307/265; 328/111

[56] References Cited
UNITED STATES PATENTS

| | | | |
|---|---|---|---|
| 3,427,478 | 2/1969 | Etter | 331/78 X |
| 3,573,652 | 4/1971 | Charters | 331/78 |
| 3,810,039 | 5/1974 | Fein | 331/78 |

*Primary Examiner*—Siegfried H. Grimm
*Attorney, Agent, or Firm*—Merchant, Gould, Smith, Edell, Welter & Schmidt

[57] ABSTRACT

Behavior modification method involving the use of a portable random interval signal generator. One disclosed embodiment has an increasing probability of obtaining a signal through a time interval. In another disclosed embodiment the probability of obtaining a signal remains constant with time. The method involves analyzing behavior at randomly occurring intervals and in a preferred form recording instances of predefined behavioral classes on a pair of counters associated with the interval generator. Another method involves providing feedback to the subject in the form of reinforcing or punishing events.

10 Claims, 8 Drawing Figures

RANDOM INTERVAL GENERATORS AND METHOD OF BEHAVIOR MODIFICATION USING SAME

BACKGROUND OF THE INVENTION

In many scientific and medical fields circumstances occur in which it is desired to sample data at random intervals so as to develop an overall statistical picture. Often, measurements which are periodic in nature are erroneously treated as random, resulting in gross distortions in the statistical analysis.

For example, one field in which random sampling has proved to be extremely useful is the field of psychology which deals with behavior analysis and modification. If observations of a subject's behavior are made at intervals which are random, after a sufficient number of samples, a true picture of the subject's behavior begins to emerge. However, if the measurements are periodic or partly so, rather than being truly random, great biases can result. Particularly important errors can be made when the observer erroneously thinks that the measurements are being made randomly and is unaware of their periodic or event contingent nature. For example, if a subject is observed at certain times each day, e.g. hourly on the hour, the observed behavior may well be more indicative of customary or habitual behavior at the beginning of appointments (which often begin hourly) rather than providing an indication of behavior in general. Even more seriously, the subject may learn to anticipate the observations, thereby giving biased data.

In order for sampling techniques to provide unbiased estimates, the samples must be taken at truly random intervals, and not at periodic intervals or at observer chosen intermittent intervals which the observer subjectively feels are random. This is because what the observer subjectively feels is random may in fact represent, unknown to the observer, a periodic factor relating to the observer's own behavior or state of awareness. Clearly this method of taking data would add unspecified biases and distortions to the data. An independent and objective means of generating random time intervals is needed.

A number of random and pseudo random devices have been proposed for this purpose in the prior art. One class of prior art devices uses an endless tape loop or program disc which has a fixed number of randomly spaced marks for triggering an alarm as they are moved past a sensor. Such devices are only pseudo random because eventually the pattern will repeat and the subject may become subconsciously aware of the pattern. Other prior art devices have used various types of electronic circuits with varying degrees of success at achieving a true random function. Some of such prior art devices are either too complex to be conveniently portable, or too costly for widespread applicability. In certain types of behavior analysis and modification described herein, a highly portable random interval generator which is so small and convenient that it does not interfere with ordinary activities is essential.

Behavior analysts have used prior art devices to cue sampling of an individual's behavior. For example, the time study engineer (either directly or photographically) may observe a machine operator and record by tallying appropriate categories whether the operator was engaged in one activity or another at the instant of the cue. After a sufficient number of samples, the portion of time the operator spent engaged in each category of activity may be reliably estimated. While truly randomly spaced cues are preferable even in this procedure, one form of bias is eliminated since the operator does not know at what instant he was observed, so he can not learn to predict when the next intermittent sample will be taken.

In order for an observer to analyze the behavior of a subject over the wide ranging course of the subject's daily behavior (a distinctly different problem from observing a machine operator at his post), the apparatus for generating random intervals must be conveniently portable. A further requirement for long term in vivo monitoring is a method of recording the appropriate tallies which is portable and maximally convenient for the observer. Furthermore, it should be possible to record tallies only at appropriate times, that is, when the signal sounds, to prohibit accidental recording. These requirements are particularly important when the observer analyzes his own behavior so that the act of recording minimally alters his own environment and he is prevented from biasing the observations by recording tallies without his having received the signal.

A well-known principle of behavior modification is that, if a reinforcing event follows temporally an instance of a particular class of behaviors, the relative frequency of that behavioral class will increase. Furthermore, if a punishing event follows temporally an instance of a particular behavioral class, that class' relative frequency will decrease. A wide variety of events may serve as reinforcers if the subject is properly trained: examples are a particular sound, presentation of a light of a particular color, etc. Very often, one of the best reinforcers is objective numerical feedback of the number of prior successes. Analogously true is the variety of punishing events.

It is widely accepted that it is difficult for an individual to apply the rules of reinforcement and punishment to his own behavior, since their application requires the individual to withhold reinforcement from himself until his behavior meets a particular criterion. Randomly cued presentation of either a reinforcing or a punishing event, the choice between the two depending on the observed recent stream of events, obviates the aforementioned difficulty, and is conceptually markedly different from the prior art operant conditioning rules.

SUMMARY OF THE INVENTION

According to one aspect of the present invention, a portable operator resettable random interval generator is provided. Circuit means are provided for generating a time interval of random length. Signal means produce a continuous alerting signal at the conclusion of a time interval. Two or more operator actuated reset means are provided, each coupled to terminate the alerting signal and start the generating means on the next time interval. Feedback means coupled to the reset means provide distinctive feedback to the operator, according to which of the reset means was actuated.

According to a preferred embodiment, the feedback means may comprise registers which are enabled by the signalling means, and are selectively incremented by the appropriate reset means.

According to another aspect of the present invention, there is provided a random interval generator having an equal probability that the alarm will occur at any time from the start (or from a predetermined minimum interval) to a known maximum interval. Accordingly, the probability that the alarm will occur in the next instant of time increases throughout the interval. This device comprises a counter, an alarm, operator activated means for resetting the alarm, and means for producing relatively fast and slow trains of pulses. The slow pulses are fed into the counter which gradually accumulates an increasing count. At a predetermined count, the alarm is triggered. From this point until the alarm is reset by the operator, the high frequency pulses are fed into the counter which repeatedly fills, resets to zero, then fills again. When the operator acts to reset the alarm, the counter is stopped and contains a random number at that point. Counting then continues with the slow pulses from the random number on up to the predetermined number. The frequency of the high frequency pulses is made high enough so that the counter is cycled to full count and reset a number of times during the period of variability of the reaction time of the operator's resetting of the alarm. This assures that the number preloaded into the counter will be for all intents and purposes a random number.

Another type of random interval generator according to the present invention has a constant probability, at any given instant, that an alarm will occur in the next instant. Thus, for this type of generator, the probability density for different interval lengths is a decreasing function for increasing interval lengths. A noise generator is used to randomly vary the period of an oscillator, and a high frequency oscillator produces pulses of much greater frequency than those produced by the variable period oscillator. A logic gate selectively transmits pulses from the high frequency oscillator to a counter, in response to pulses from the variable period oscillator. Detection means are provided for comparing the count in the counter with a predetermined value. A clock alternately enables the gate and disables the detection means; then disables the gate and enables the detection means. The variable period oscillator allows the high speed pulses to fill and reset the counter many times before the variable speed oscillator stops the counter at a random number. Eventually the clock enables the detection means. If the number contained in the counter exceeds the predetermined value, an alarm signal is generated; otherwise the cycle is repeated.

According to another aspect of the invention, a method of behavior analysis is provided which is a marked extension of prior art methods. The method makes use of a portable random interval signal generator having a pair of reset means each connected to its own counting register. Two behavioral categories are predefined, and each category is assigned to one of the reset means and its associated register. A random interval signal is generated, and behavior at the time of the signal is monitored. The monitored behavior is then compared to the predefined categories, and the corresponding reset means is actuated, thus incrementing the appropriate counter. The portability of the device employed enables the analysis to be performed throughout a normal day's activity for the subject. The method can be performed by an observer of a subject or the observer can be the subject.

According to another aspect of the invention there is provided a method of behavior modification which is an extension of the behavior analysis method above. This method makes use of a portable random interval signal generator having a pair of reset means coupled to feedback means for providing distinctive reinforceing or punishing events, according to which of the reset means is activated. Two behavioral categories are predefined, and one of the pair of reset means and its connected feedback means is assigned to each category. A random interval signal is generated, and behavior is monitored at the time of the signal. The monitored behavior is compared against the predefined categories and the appropriate reset means is actuated, thus initiating the appropriate reinforcing or punishing feedback.

DESCRIPTION OF THE PREFERRED EMBODIMENTS

Figure 1:
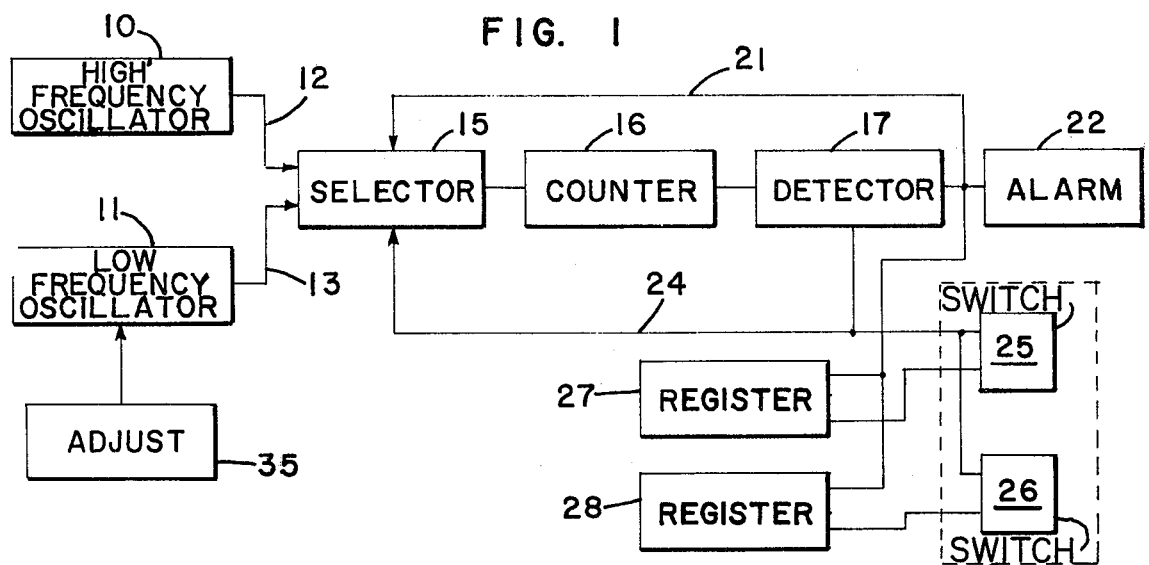
FIG. 1 is a block diagram of a random interval generator according to the present invention.

In FIG. 1, a high frequency oscillator 10 and a low frequency oscillator 11 are connected by leads 12 and 13, respectively, to inputs of a selector circuit 15. The output of selector 15 connects to the input of the counter 16. A detector 17 is connected to counter 16, and also connects through lead 21 to an alarm or signalling device 22. Lead 21 from detector 17 also connects back to the selector 15. An operator actuable reset device 23 connects via lead 24 to detector 17 and to selector 15.

The terms "high frequency" and "low frequency" as applied to oscillators 10 and 11 are not used in an absolute sense to imply frequency bands, but rather are used only in a relative sense. Thus, the output frequency of oscillator 10, also called the randomization oscillator, is considerably higher in frequency than that of oscillator 11.

Selector 15 functions as a switch for selectively coupling high frequency pulses from lead 12 or 13 to the counter. Control signals applied to selector 15 by leads 21 and 24 control the switching action of the selector. When detector 17 changes states, as explained hereinafter, a signal on lead 21 causes selector 15 to couple the high frequency oscillator to the counter. When the reset device 23 is activated, a signal on lead 24 causes selector 15 to couple the low frequency oscillator to the counter.

Counter 16 is a conventional digital counter having a maximum count N. After counter 16 has filled to the full count N, the next pulse resets the counter to zero. Detector 17 monitors the count in counter 16, and changes states when a predetermined number is reached. In the preferred embodiment, detector 17 is designed to change states when the counter reaches a full count, but other counts could be used if desired. Upon changing states, detector 17 energizes the alarm device 22 and switches selector 15. Detector 17 remains locked in this state regardless of the fact that counter 16 may no longer contain a full count, until detector 17 is reset by the reset device 23. The alarm or signalling device 22 may be a simple buzzer or beeper to alert the user that a time interval has been completed.

The reset device 23 may take several forms. In its simplest form, reset device 23 may be a simple operator actuated switch for performing the functions outlined above. In the embodiment shown in FIG. 1, reset devices 23 comprises a pair of operator actuated switches 25, 26, both of which are connected to lead 24 for performing the reset functions described above. In addition, switches 25 and 26 are connected to a pair of registers 27 and 28, respectively, for counting the number of times that each switch is activated. Registers 27 and 28 may be any type of mechanical or electronic counter as desired, and preferably include some type of readout devices so that their count may be determined. Preferably, registers 27 and 28 are not enabled until the alarm or signalling devices has been energized, and this is accomplished by the enabling lead 21 which connects registers 27 and 28 to the output of detector 17. Switches 25 and 26, and registers 27 and 28 are useful in recording instances of positive and negative behavior at random intervals, according to the method of the present invention.

Figure 2:
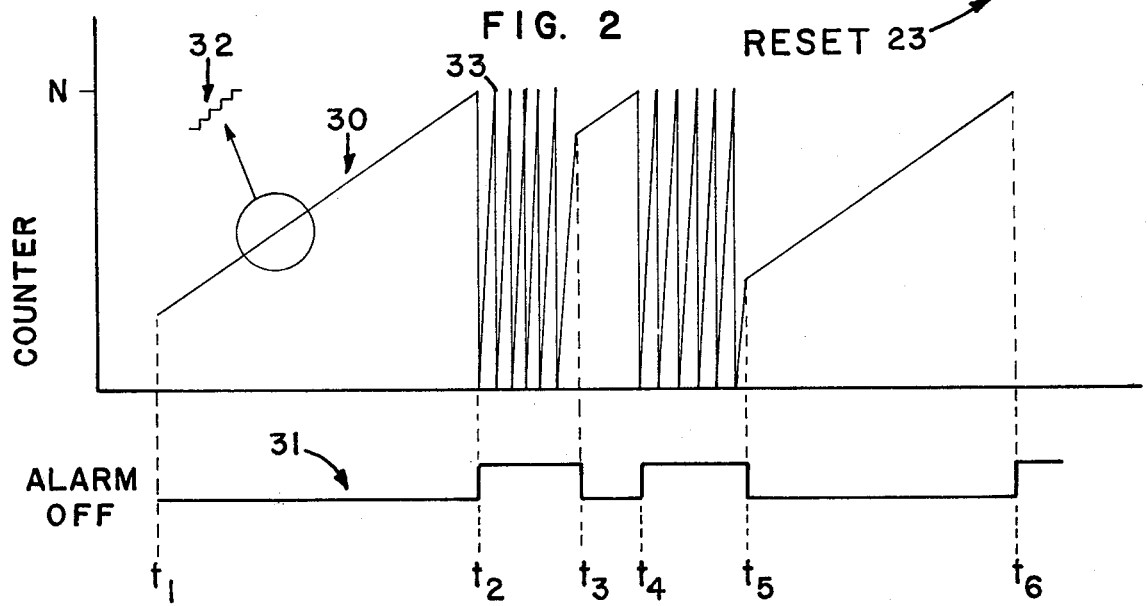
FIG. 2 is a graph of wave forms illustrating the operation of the circuit of FIG. 1.

Referring to FIG. 2, a pair of wave forms are shown. The horizontal axis represents time and the vertical axis indicates the count in counter 16 at a given time. Wave form 31 shows the ON and OFF periods of the alarm of signalling devices 22. During the time interval from $t_1$ to $t_2$ the low frequency oscillator is connected to counter 16 and is slowly building up the count therein. Thus, during this time interval wave form 30 shows a gradually increasing value, whose slope is determined by the frequency of the low frequency oscillator. For purposes of clarity, the slope of wave form 30 is shown as being a straight line, but in fact it is a stair step of discrete increments as indicated by detail 32. During this time period, the alarm is OFF as indicated by wave form 31.

At time $t_2$ the counter reaches its predetermined number (in this embodiment the full count of N) causing detector 17 to change states. Alarm device 22 is then turned ON as indicated by wave form 31 at time $t_2$. At the same time, the high frequency oscillator is switched into counter 16. Since this counter has a much higher frequency, it causes counter 16 to fill and reset very rapidly in a short time interval. Point 33 in FIG. 2 shows the time of the first such filling of counter 16 after switching to the high frequency oscillator. The slope of wave form 30 from time $t_2$ until point 33 is reached represents the frequency of the high frequency oscillator, which is much greater than the slope of the low frequency oscillator wave form.

At time $t_3$ the operator has responded by activating the reset device 23. This immediately turns off the alarm and switches selector 15 from the high to the low frequency oscillator causing wave form 30 to switch from the high slope to the low slope. The number stored in the counter at time $t_3$ is a random number between zero and N. This is because the time interval $t_2$ and $t_3$ is dependent upon the reaction time of the operator. Generally, this interval will be several seconds, and the variability of the reaction time interval will be about half a second. The frequency of the high frequency oscillator is sufficiently high that the counter is filled and reset a number of times during the period of variability of the interval. Thus, when the reset occurs at time $t_3$ the instantaneous count in counter 16 may be at any value. It is for this reason that the high frequency oscillator 10 is referred to as the randomization oscillator, since it preloads a random number into the counter.

From time $t_3$ to $t_4$ counting continues under control of the low frequency oscillator. At time $t_4$ the number N is reached again and the chain of events described above with reference to time $t_2$ to $t_3$ repeats for the time interval $t_4$ to $t_5$. At time $t_5$ the reset occurs again, this time with yet another number preloaded into counter 16.

Thus, the time intervals $t_1$–$t_2$, $t_3$–$t_4$ and $t_5$–$t_6$ are all of random length, the length being determined by the random number preloaded into the counter at the beginning of the interval. The frequency of the high frequency oscillator is so great that even slight variations in the reaction times $t_2$–$t_3$ and $t_4$–$t_5$ will have a drastic effect on the random number preloaded into the counter.

It is desirable to provide a frequency adjusting means 35 (see FIG. 1) connected to the low frequency oscillator 11 for adjusting the frequency thereof. In this manner the slope of the wave form from $t_1$ to $t_2$ can be adjusted, and the maximum possible time interval from a count of N can be adjusted. The usefulness of this feature will become more apparent hereinafter in the description of the method according to the present invention.

In one preferred embodiment according to FIG. 1, oscillator 11 was selected to run at a frequency programmable from 0.5 hz. to 100 hz. The randomization oscillator was set to run at about 1 MHz, and the counter had a capacity N of about $2^{13}$. If $F_s$ is the frequency of (slow) oscillator 11, and $F_f$ is the frequency of (fast) oscillator 10, then random operation will be assured if $N/F_f$ is much smaller than the variablity of reaction time. If this relationship holds, then the counter setting $N_r$ at the time the opertor resets the device will be selected with essentially uniform probability distribution. The length of the following random interval will be $N-N_r/F_s$, which will also be uniformly distributed.

It will be appreciated that the time base in FIG. 2 has been intentionally distorted for purposes of clarity. Because of the great disparity between the frequencies of the high and low frequency oscillators, the time base during the randomization periods $t_2$–$t_3$ and $t_4$–$t_5$ has been stretched, while the time base curing the random intervals $t_1$–$t_2$, $t_3$–$t_4$, and $t_5$–$t_6$ has been compressed.

In some cases it may be desirable to insure that a minimum time interval will be guaranteed even though the counter begins the interval at nearly maximum count. This can be accomplished by putting a delay circuit, for example, between the detector and the alarm, or between the reset and enabling of the low frequency oscillator.

Figure 3:
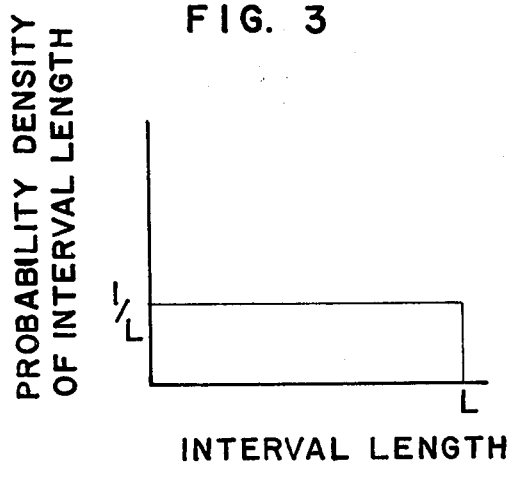
FIGS. 3 and 4 are probability distribution functions for the embodiment of FIG. 1.

Referring now to FIG. 3, the probability density of interval length is plotted as a function of interval length. The maximum interval length L equals N divided by $F_s$ and corresponds to a case in which the randomly chosen number stored in the counter was zero. FIG. 3 shows that there is a uniform probability that an interval will be of any given length between zero and L. Of course, the maximum interval L can be adjusted by changing the frequency $F_s$ since it is a function thereof.

Figure 4:
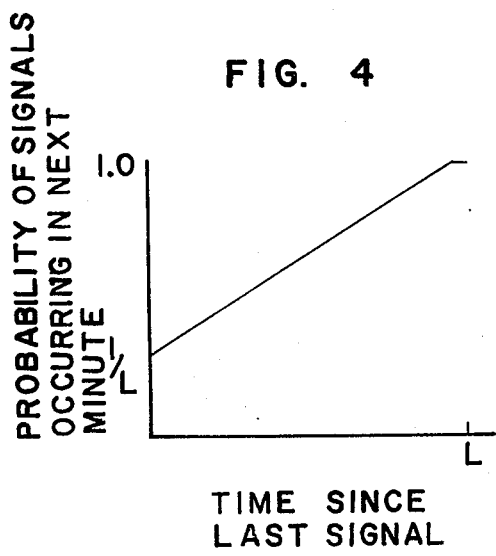

FIG. 4 shows the probability that a signal will occur in the next increment of time as a function of the time since the last signal. During the first increment of time, the probability of a signal is $1/L$, as in the graph of FIG. 3. If no signal is obtained, then the probability that the signal will occur in the next increment of time is increased, and so on until just before the time $L$, if no signal has yet been reached, the probability is one that the signal will occur at time $L$.

Figure 5:
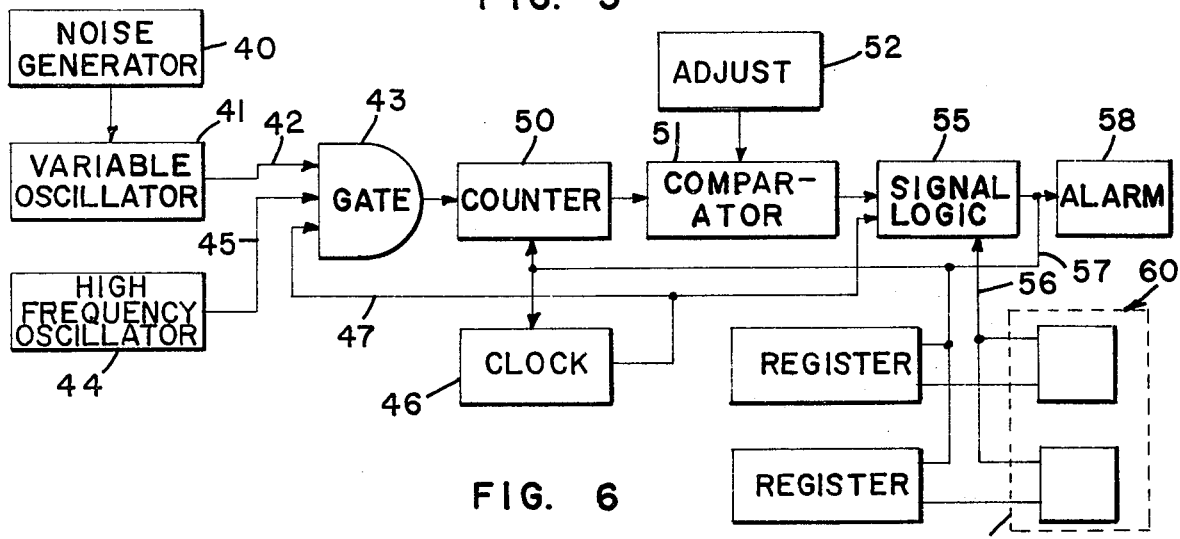
FIG. 5 is a block diagram of a constant probability random interval generator according to the present invention.

Referring now to FIG. 5, there is shown a block diagram for a constant probability random interval generator according to the present invention. A noise generator 40 is connected to and randomly alters the period of a variable period oscillator 41. The output of oscillator 41 connects via lead 42 to AND GATE 43. A high frequency oscillator 44 is also connected to an input of AND GATE 43, by lead 45. A third input to AND gate 43 is generated by a clock circuit 46, whose output connects to lead 47.

The output of AND gate 43 connects to a digital counter 50, which in turn is connected to a comparator 51. Comparator 51 is adjustable as indicated by adjustment means 52 connected thereto.

Comparator 51 serves as a detection means for determining when the count in counter 50 exceeds a predetermined value. The predetermined value is determined by adjustment means 52, and can be reset as desired. Comparator 51 may thus be any known type of programmable digital comparator.

Signal logic 55 receives inputs from comparator 51, from clock 46, and from lead 56 from operator actuated reset device 60. Signal logic 55 produces output signals on lead 57 which are distributed to an alarm or signalling device 58 and to clock 46 and counter 50. The function of signal logic 55 is described in detail below.

The reset means 60 may take the same form as the reset means 23 of FIG. 1. That is, reset means 60 may be a single switch connected to the signal logic, or it may comprise a pair of operator actuated switches and registers as shown, and as described above with reference to FIG. 1. As was the case in FIG. 1, each reset button in FIG. 5 serves to turn off the alarm signal, and to increment its associated counter. To prevent erroneous counts, the counters are not enabled until the alerting signal on lead 57.

Figure 6:
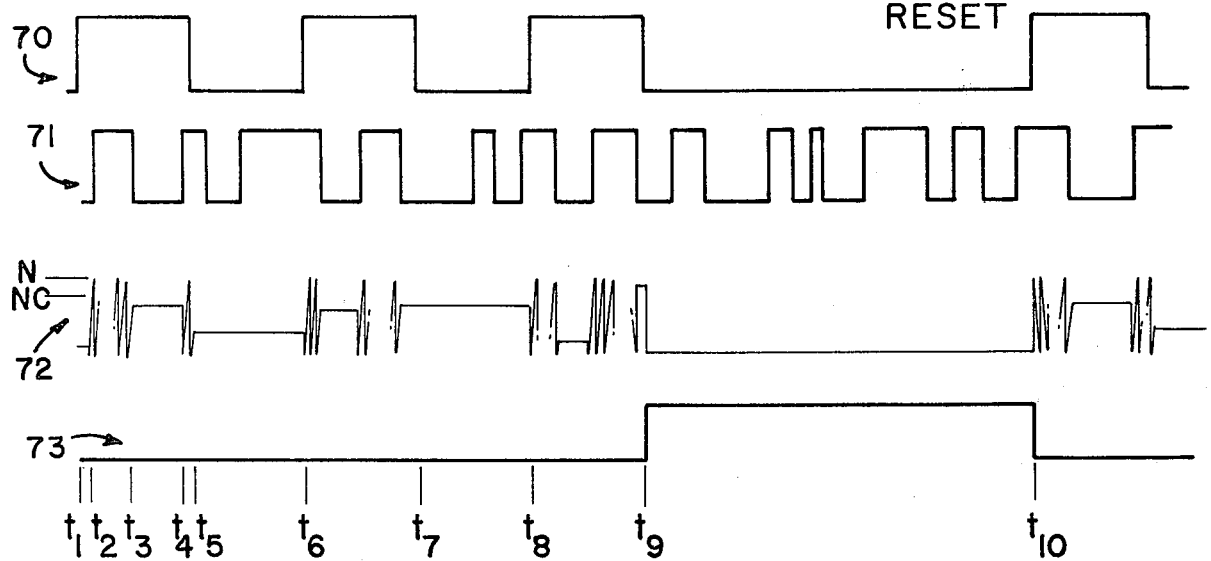
FIG. 6 is a graph of wave forms illustrating the operation of the circuit of FIG. 5.

Referring now to FIG. 6, the operation of the constant probability embodiment of FIG. 5 will now be explained. In FIG. 6, the horizontal axis represents time and four separate wave forms are shown on the vertical axis. Wave form 70 shows the output of clock 46, on lead 47. Wave form 71 shows the output of the variable period oscillator 41, from lead 42. Wave form 72 shows the count occurring in counter 50 at any given time. Wave form 73 shows the output of the alarm or signal device 58.

As indicated by wave form 71, the frequency of the variable oscillator 41 is continuously and randomly modulated by the noise generator 40. This output signal, together with the clock pulse is used to gate pulses from the high frequency oscillator into the counter. The capacity of the counter $N$, and the frequency of the high frequency pulses, $F_f$ are chosen so that the quotient $N/F_f$ which is the time required to fill the counter once, is much smaller than the standard deviation of the period of variable oscillator 41. If this relation holds, the counter will be cycled numerous times before it is gated off, and it will be gated off containing a randomly selected number. When the clock changes states, the gate is inhibited and the comparator and signal logic check to see whether the random number stored in the counter exceeds $N_c$ the predetermined criterion value. Since the number in the counter is randomly selected, there is a constant probability $1-N_c/N$ that the number will exceed the predetermined value. If so, the alarm is activated, ending the time interval.

In FIG. 6, the clock pulse 70 has just switched to its first state, going positive, at time $t_1$. A short interval later, at time $t_2$ wave form 71, which is the output from variable oscillator 41, goes positive thus enabling gate 43. From time $t_2$ to time $t_3$ both the clock and the variable oscillator signals are positive thereby enabling high frequency pulses from oscillator 44 to continually fill and reset counter 50. Wave form 72 between time $t_2$ and $t_3$ illustrates numerous such counter cycles.

At $t_3$ variable oscillator 41 changes state thereby inhibiting gate 43. The counter then contains a random number which is carried over to time $t_4$ at which time variable oscillator 41 allows further cycling of the counter.

At time $t_5$ the clock changes state thereby inhibiting gate 43, and enabling signal logic 55. However, at this time, the random number in the counter is less than the preset value $N_c$ so no alarm is sounded.

At $t_6$ the clock again changes states allowing further cycling of the counter, when the output of the variable oscillator 41 is in the proper state. At $t_7$ the clock again changes states to find another number loaded in the counter. In this instance, the counter was already inhibited shortly before $t_7$ by the changing of state of wave form 71. Form time $t_8$ to $t_9$ the clock pulse again allows cycling of counter 50. At $t_9$ when the clock changes states, the counter contains a number greater than the preset value $N_c$. With the signal logic 55 enabled, the signal from the comparator indicating the number higher than the preselected value causes the signal logic to trigger the alarm device 58, as indicated by wave form 73 at $t_9$. The signal logic also clears counter 50 and inhibits clock 46 during this time.

At time $t_{10}$ the operator has responded by activating the reset means 60 which unlatches the signal logic so as to turn off the alarm and restart the clock.

Thus, during a first half cycle of the clock a random number is loaded into the counter, under control of the variable period oscillator. During the second half cycle of the clock, a comparison and decision is made as to whether the number in the counter exceeds the preset number. If so, the alerting means is activated; if not, the cycle is repeated. Since the number loaded into the counter is randomly selected, given the restraints outlined above, the probability of getting a signal is constant, equals $1-N_c/N$; and does not depend upon how long it has been since the previous signal.

By reprogramming the comparator 51 to compare for a different predetermined value, the probability on a given decision can be adjusted. By adjusting the frequency of the clock, the time interval between two given decisions can be adjusted.

Figure 7:
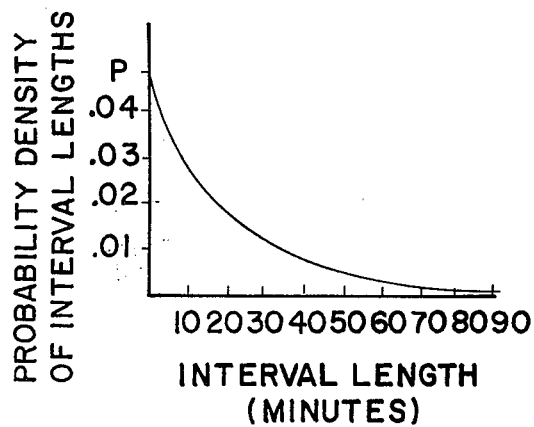
FIGS. 7 and 8 are probability distribution functions for the circuit of FIG. 5.

Referring now to FIG. 7, the probability density of interval lengths is plotted as a fuunction of interval lengths, with a probability of obtaining an alarm at any given decision time (clock pulse) of 0.05. It will be observed that the probability of obtaining a interval of a certain length decreases for longer lengths.

Figure 8:
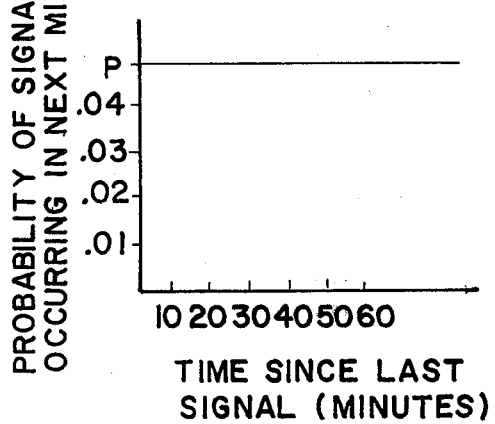

FIG. 8 shows the probability that a signal will occur in the next time increment, as a function of the time since the last signal. It will be observed that this probability is a constant 0.05, in the example given, and does not depend at all on the time since the last signal. FIGS. 7 and 8 for the embodiment of FIG. 5 should be compared against FIGS. 3 and 4, respectively, for the embodiment of FIG. 1.

The two random interval generators described above are simple but highly effective, and have wide applicability to many types of scientific endeavors. In particular, the constant probability or increasing probability features, and the easy adjustments thereof, will be very useful in critical applications where particular types of random intervals are required. Depending upon the application and field of use, either generator can be reset by a human operator, or a human or animal test subject; or by a machine, electronic device or other apparatus associated with the generator in a particular application.

In addition to general applicability, the random interval generators according to the present invention are especially applicable in carrying out the method of the present invention, which is behavior analysis and modification.

The method of behavior analysis to be described is a marked extension of prior art methods enabled by the portability of the interval generating apparatus and the self-containment of the tallying apparatus.

An observer observes the behavior of a subject (the subject and observer may be the same individual). The observer has predefined two categories of the subject's behavior. The observer carries a device which, at the end of random intervals, simultaneously emits a signal and enables two reset means. One reset means is associated with each of the two behavioral categories. At each signal the observer decides which one of the two predefined categories describes the current behavior and actuates the appropriate reset means. Since the two reset means are each connected to counters, selecting the appropriate reset means records a tally in the appropriate counter. This running count in the two counters may be used in a variety of ways; for example, the ratio of counts in one counter to the other can provide an estimate of the relative frequency of instances of occurrence of the predefined behavioral categories.

The method of behavior modification is an extension of the above described method of behavior analysis. The observer observes the behavior of the subject (who may be himself), and has predefined two behavioral categories. At random intervals, supplied by the apparatus, the signal indicates that one of the two reset means must be actuated to terminate the signal. Each reset means terminates the signal and delivers to the subject a different and distinct reinforcing or punishing event. One example of a reinforcing event is the increment of a counter which has previously been defined as good; analogously, the increment of a counter previously defined as bad is an example of a punishing event. Other reinforcing or punishing events may be used, for example, delivery of a mild electric shock to the subject might be an appropriate punishing event.

I claim:

1. An operator resettable random interval generator, comprising:
  a. means for generating a time interval of random length;
  b. signal means connected to said generating means for producing an alerting signal at the conclusion of a generated random time interval;
  c. a pair of operator actuated reset means each connected for terminating said signal and initiating the next random time interval; and
  d. feedback means connected to said pair of reset means for providing distinctive feedback to the operator, according to which of the reset means was actuated.

2. Apparatus according to claim 1 wherein said feedback means comprises a pair of counters, and wherein said distinctive feedback comprises the count of how many times each of said reset means has been actuated.

3. A resettable random interval generator, comprising:
  a. means for producing a first train of pulses;
  b. means for producing a second train of pulses having a frequency much higher than said first train of pulses;
  c. a counter;
  d. a switching means connected for selectively coupling said first or second train of pulses to said counter;
  e. signal means connected to said counter for producing an alerting signal when said counter reaches a predetermined count, said signal means further connected to said switching means;
  f. reset means connected to said signal means for turning off said signal means, said reset means further connected to said switching means; and
  g. said switching means operable to couple said first train of pulses to said counter upon activation of said reset means, and operable to couple said second train of pulses to said counter upon activation of said signal means, whereby said second train of pulses runs said counter to a random count dependent upon the time between the alerting signal and the operation of the reset means, and whereby said first train of pulses runs said counter to the predetermined count, thereby producing a random length time interval to the next alterting signal.

4. Apparatus according to claim 3 whereby said reset means includes a pair of registers and operator actuated means for selectively incrementing either register.

5. Apparatus according to claim 3 wherein said means for producing a first train of pulses comprises an adjustable frequency oscillator, whereby the average duration of said random intervals can be adjusted.

6. Apparatus according to claim 3 further including time delay means connected between said counter and said signal means for delaying for a predetermined time the alerting signal when said counter reaches a predetermined count, thereby assuring a predetermined minimum time interval.

7. A constant probability random interval generator, comprising:
  a. a noise generator;
  b. a variable period oscillator connected to said noise generator, said oscillator operable to produce pulse of randomly varying period according to the random characteristics of said noise generator;
  c. a high frequency oscillator for producing pulses of much greater frequency than those produced by said variable period oscillator;
  d. a counter;
  e. a logic gate connected to said variable period oscillator, said high frequency oscillator and said counter, said logic gate operable to alternately block or transmit pulses from said high frequency oscillator to said counter in response to pulses from said variable period oscillator;

f. detection means connected to said counter and operable when enabled to compare the count in said counter with a predetermined value; and g. clock means connected to said gate means and said detection means for enabling said gate and disabling said detection means in a first state, and for disabling said gate and enabling said detection means in a second state.

8. Apparatus according to claim 7 further including signal means connected to said detection means for producing an alerting signal when the compared count exceeds said predetermined value, and further including reset means for turning off the signal means.

9. Apparatus according to claim 8 wherein said reset means comprises a pair of registers and operator actuated means for selectively incrementing either register.

10. Apparatus according to claim 8 further including time delay means connected between said detection means and said signal means for delaying the alerting signal for a predetermined time, thereby assuring a predetermined minimum time interval.

* * * * *